(12) United States Patent
Murray et al.

(10) Patent No.: US 8,674,041 B2
(45) Date of Patent: Mar. 18, 2014

(54) LOW TEMPERATURE CURE USING BENZOPINACOL POLYMERIZATION INITIATOR

(75) Inventors: Thomas James Murray, Chesterfield, MO (US); David L. Vines, Imperial, MO (US)

(73) Assignee: Elantas PDG, Inc., St. Louis, MO (US)

( * ) Notice: Subject to any disclaimer, the term of this patent is extended or adjusted under 35 U.S.C. 154(b) by 67 days.

(21) Appl. No.: 13/554,235

(22) Filed: Jul. 20, 2012

(65) Prior Publication Data
US 2013/0190467 A1 Jul. 25, 2013

Related U.S. Application Data

(60) Provisional application No. 61/510,528, filed on Jul. 22, 2011.

(51) Int. Cl.
*C07F 7/28* (2006.01)
*C07F 7/00* (2006.01)
*C08F 22/10* (2006.01)

(52) U.S. Cl.
CPC ... *C07F 7/28* (2013.01); *C07F 7/00* (2013.01); *C08F 22/10* (2013.01)
USPC ........... 526/172; 526/113; 526/319; 526/321; 556/54

(58) Field of Classification Search
CPC .................................. C07F 7/00; C07F 7/728
USPC .............. 502/152, 156, 171, 172; 556/52, 54; 526/120, 170, 172, 319, 312, 113, 321
See application file for complete search history.

(56) References Cited

U.S. PATENT DOCUMENTS

| 4,336,366 A | 6/1982 | Berner |
| 2010/0217016 A1 | 8/2010 | Lejeune |

FOREIGN PATENT DOCUMENTS

| EP | 0 411 937 A2 | 2/1991 |
| WO | WO 2006/023785 A2 | 3/2006 |

OTHER PUBLICATIONS

International Search Report, Form PCT/ISA/210, mailed Feb. 1, 2013, for corresponding PCT International Patent Application No. PCT/US2012/047607.
Written Opinion, Form PCT/ISA/237, mailed Feb. 1, 2013, for corresponding PCT International Patent Application No. PCT/US2012/047607.

*Primary Examiner* — Caixia Lu
(74) *Attorney, Agent, or Firm* — Curatolo Sidoti Co., LPA; Salvatore A. Sidoti; Joseph G. Curatolo

(57) ABSTRACT

A polymerization initiator for reactive monomers and unsaturated polymers which is the reaction product of a metal-organic titanium compound or a metal-organic zirconium compound and pinacol compound is disclosed. Further disclosed are methods for preparing the polymerization initiator and using the polymerization initiator for low temperature curing.

23 Claims, No Drawings

LOW TEMPERATURE CURE USING BENZOPINACOL POLYMERIZATION INITIATOR

CROSS-REFERENCE TO RELATED APPLICATIONS

This application claims the benefit of the filing date, under 35 U.S.C. §119(e), from U.S. Provisional Application Ser. No. 61/510,528, filed Jul. 22, 2011, which is hereby incorporated by reference.

TECHNICAL FIELD

The present disclosure relates to polymerization initiators for reactive monomers and unsaturated polymers. The present disclosure more particularly relates to polymerization initiator systems that are based on benzopinacol that can be used in curing unsaturated polymers and/or monomers at low temperatures.

BACKGROUND

Organic peroxides are the industry standard for polymerizing unsaturated polyester resins. Depending on the peroxide structure, cure can be achieved at room temperature to elevated temperatures of 180° C. The desire to cure at low temperature (below 120° C.) is almost uniformly desired. In addition to the obvious energy savings, throughput can be significantly increased by not having to raise the temperature of the article to be cured. Alternate low temperature initiating systems would include diazo compounds as well. The drawback to low temperature curing peroxides or diazo compounds is the stability of the peroxide/diazo compound. Many of the peroxides must be stored at low temperatures and shipped under refrigerated conditions. The thermal instability and handling is a well known danger to employees who use these materials.

Promoters can also be used in combination with peroxides to lower cure temperature. It is common practice to use promoters, such as cobalt, iron, and manganese derivatives to accelerate cure at low temperature. Amine, acetoacetates and amides are also used in combination with metals such as cobalt to promote peroxide decomposition and give a high radical flux needed for cure.

Benzopinacol has been known for some time as a suitable radical polymerization initiator. However, the reactivity and end product properties have not been sufficient enough to overcome the extra preparation expense compared to peroxide based radical initiators. To improve reactivity and solubility, the potassium/sodium salts of benzopinacol have been reacted with di-, tri-, and tetra chlorosilanes or polyorganosilane/siloxane materials. These products have had limited commercial success however they have never been shown to significantly lower cure temperature in unsaturated polymers.

A polyurethane derivatized benzopinacol initiator is known and was reported to behave as a "living" catalyst. The reactivity is also similar to benzopinacol itself. Similar work was shown by Chen, et. al. (European Polymer Journal, 36 (2000) 1547-1554) using monofunctional isocyanates such as phenylisocyanate. These initiators were also found to be "living" catalysts.

Bromoacetyl derivatives of benzopinacol are known as flame retardant initiators for the polymerization of unsaturated polyester (UPE) systems. Additionally, phosphorus and silyl ethers of benzopinacol as flame retardant initiators for UPE systems have been reported.

SUMMARY

Provided is a polymerization initiator comprising a pinacol, such as benzopinacol, and a metal-organic titanium or a metal-organic zirconium compound. The metal-organic titanium or zirconium compound can be used catalytically in relation to the benzopinacol.

According to certain illustrative embodiments, the polymerization initiator comprises the reaction product of a metal-organic titanium compound or a metal-organic zirconium compound and pinacol compound of the following general formula:

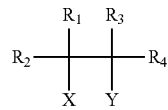

wherein $R_1$ and $R_3$ are the same or different substituted or unsubstituted aromatic groups;
wherein $R_2$ and $R_4$ are the same or different substituted or unsubstituted aliphatic or aromatic groups; and
wherein X and Y are the same or different and may comprise hydroxyl, alkoxy, or aryloxy groups.

Additionally provided is a process for preparing a polymerization initiator comprising reacting a metal-organic titanium compound or a metal-organic zirconium compound and pinacol compound of the following general formula:

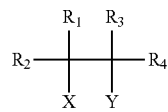

wherein $R_1$ and $R_3$ are the same or different substituted or unsubstituted aromatic groups;
wherein $R_2$ and $R_4$ are the same or different substituted or unsubstituted aliphatic or aromatic groups; and
wherein X and Y are the same or different and may comprise hydroxyl, alkoxy, or aryloxy groups.

According to certain illustrative embodiments, the process for preparing a polymerization initiator comprises preparing a titanium or zirconium alkoxide of benzopinacol, the process comprising reacting benzopinacol or a derivative of benzopinacol with a metal-organic titanium or zirconium compound that has volatile ligands, and optionally, an inert solvent.

According to certain illustrative embodiments, the titanium or zirconium alkoxide of benzopinacol comprises the following general formula:

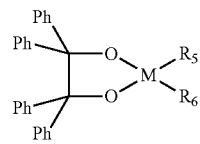

wherein M comprises titanium or zirconium; and
wherein $R_5$ and $R_6$ may be the same or different and comprise an organic moiety. According to certain illustrative embodiments the organic moiety may comprise alkyl, alkoxy, or aryl groups.

Further provided is a polymerization process comprising adding a polymerization initiator comprising of pinacol and a metal-organic titanium or zirconium compound to reactive monomer with or without an unsaturated polymer and polymerizing said reactive system.

According to certain illustrative embodiments, the polymerization process comprises separately adding (i) a metal-organic titanium compound or a metal-organic zirconium compound and (ii) a pinacol compound to a reactive monomer, or an unsaturated polymer, or a mixture of unsaturated polymer and reactive monomer; and polymerizing said reactive monomer and/or unsaturated polymer.

According to certain illustrative embodiments, the polymerization process comprises adding a metal-organic titanium compound or a metal-organic zirconium compound to a reactive monomer, or an unsaturated polymer, or a mixture of unsaturated polymer and reactive monomer to prepare a first mixture, adding a pinacol compound to a reactive monomer, or an unsaturated polymer, or a mixture of unsaturated polymer and reactive monomer to prepare a second mixture, combining said first mixture and said second mixture, and polymerizing said reactive monomer and/or unsaturated polymer present in said combined first and second mixture.

DETAILED DESCRIPTION

Disclosed is a polymerization initiator which allows low temperature cure of unsaturated systems without the use of traditional initiators, such as peroxides. The use of the present polymerization initiator system also allows for two component systems with mix ratios of any range as compared to peroxide systems where a small amount of peroxide, typically 1-3% by weight, must be mixed in the resin material.

In order to achieve low temperature cure, the process utilizes benzopinacol and a metal-organic titanium or zirconium compound as the initiator system for UPE resins containing styrene or other reactive monomers. The radical polymerization initiators used in the process allows low temperature cure without the use of peroxides when the resins are cured into articles of commerce.

The metal-organic titanium compound may include titanates such as tetrabutyltitanate, tetra t-butyltitanate, tetraisopropyltitanate, tetra n-propyltitanate, chlorotributyltitanate, dichlorodibutyltitanate, titanium di-n-butoxide (bis-2,4-pentanedionate), titanium diisopropoxide bis(ethylacetoacetate), cyclopentadienyltitanium trichloride, titanium tetrachloride, titanium tetrabromide, titanocene dichloride, alkyl substituted titanocene dichloride, alkyl substituted cyclopentadienyl titanium trimethoxide, titanium triisostearoylisopropoxide, titanium tetrakis(bis-2,2-(allyloxy-methyl)butoxide, titanium triacrylatemethoxyethoxyethoxide, cresyltitanate, phenyltitanium triisopropoxide, and titanium 3,6-dioxaheptanoate.

The metal-organic zirconium compound may include but not limited to zirconates such as tetrabutylzirconate, tetraisopropylzirconate, tetra n-propylzirconate, zirconium di-n-butoxide (bis-2,4-pentanedionate), zirconium (tetra-2,4-pentanedionate), zirconium diisopropoxide bis(ethylacetoacetate), cyclopentadienylzirconium trichloride, zirconium tetrachloride, zirconium tetrabromide, zirconocene dichloride, alkyl substituted zirconocene dichloride, alkyl substituted cyclopentadienyl zirconocene trimethoxide.

The pinacol compound that is reacted with the titanium or zirconium containing compound to produce the polymerization initiator is of the following general formula:

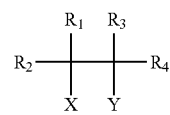

wherein $R_1$ and $R_3$ are the same or different substituted or unsubstituted aromatic groups, wherein $R_2$ and $R_4$ are the same or different substituted or unsubstituted aliphatic or aromatic groups, and wherein X and Y are the same or different and may comprise hydroxyl, alkoxy, or aryloxy groups. According to certain illustrative embodiments, the pinacol compound comprises benzopinacol where each of $R_1$-$R_4$ are phenyl rings.

According to certain illustrative embodiments, one or more of the phenyl rings on the benzopinacol molecule may be substituted. For example, and without limitation, one or more of the phenyl rings on the benzopinacol molecule may include alkyl, aryl, alkoxy, halogen substitutions which provide derivatives of benzopinacol that function as free radical initiators for polymerization of unsaturated polyester resins with reactive monomers such as styrene or acrylates.

A titanium alkoxide of benzopinacol may be prepared by reacting benzopinacol with tetraalkyltitanate. The tetraalkyltitanate may be dissolved in an inert solvent. According to certain illustrative embodiments, the tetraalkyltitanate or other titanate with leaving groups may comprise tetrabutyltitanate, tetra t-butyltitanate, tetraisopropyltitanate, tetra n-propyltitanate, chlorotributyltitanate, dichlorodibutyltitanate, titanium di-n-butoxide (bis-2,4-pentanedionate), titanium diisopropoxide bis(ethylacetoacetate), cyclopentadienyltitanium trichloride, titanium tetrachloride, titanium tetrabromide, titanocene dichloride, titanium triisostearoylisopropoxide, titanium tetrakis(bis-2,2-(allyloxy-methyl)butoxide, titanium triacrylatemethoxyethoxyethoxide, cresyltitanate, phenyltitanium triisopropoxide, and titanium 3,6-dioxaheptanoate. The tetrabutyltitanate (1 mol) may be dissolved in an inert solvent, such as toluene. There is no limitation on the type of solvent or combinations of solvents that may be used in the process for preparing the titanium alkoxides of benzopinacol and other solvents may be used as long as they are nonreactive. Benzopinacol (1 mol) and another mono, di-, or tri-functional alcohol (ROH, 0-1 mol) is added to the dissolved tetraalkyltitanate. The mixture is subjected to vacuum distillation (rotary evaporator) to remove the solvent under reduced pressure. The process is continued until the solvent and butyl alcohol were removed.

According to certain illustrative embodiments, the process for preparing a titanium alkoxide of benzopinacol comprises the following general reaction scheme:

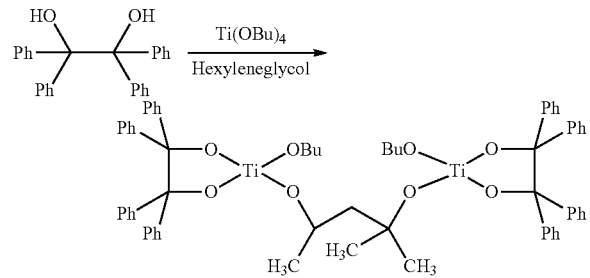

According to certain illustrative embodiments, the process for preparing a zirconium alkoxide of benzopinacol comprises the following general reaction scheme:

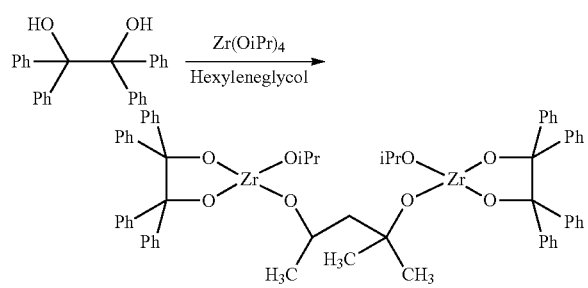

A wide variety of polyols can be used in the process of the preparation of the titanium alkoxide of benzopinacol and zirconium alkoxide of benzopinacol initiators. Suitable polyols include common diols such as ethylene glycol, propylene glycol, 1,3-propanediol, 1,4-propanediol, 1,4-butanediol, 2,2-dimethyl-1,3-propanediol, 2-methyl-1,3-propanediol, glycol ethers such as diethylene glycol and dipropylene glycol, and polyoxyalkylene glycols like polyoxyethylene glycol and polyoxypropylene glycol. Triols and higher functional polyols such as glycerol, trimethylol propane and oxyalkylated adducts thereof can also be used. Preferably, the polyols are aliphatic or alicyclic and optionally contain C—O—C linkages.

Examples of oils containing unsaturation include castor oil, peanut oil, linseed oil, safflower oil, olive oil, cotton oil, rapeseed oil, soybean oil, and tung oil, and mixtures thereof. In addition, fatty acids could be used in combination with or instead of the oil. An example would be ricinoleac acid instead of castor oil. Modified oils such as epoxidized soybean oil may also be used.

It is well known how unsaturated polyester resins can be synthesized. The progress of the reaction can be followed by measuring the acid value of the mixture. Glycols are added along with unsaturated diacids that include maleic anhydride and the mixture is heated to 355-430° F. with some form of agitation such as stirring. Dicyclopentadiene can also be added with cracking (Diels-Alder chemistry) or under hydrolysis conditions to add to the polymer. Volatiles are removed, for example, by distillation and the acid value (ASTM D1639-90) and viscosity (ASTM D1545-89) of the mixture are monitored until the desired end-point is reached. In addition the reaction with the glycols can be carried out in the presence of oils containing ethylenic unsaturation such as soybean oil. The reaction mixture is cooled and monomer is added to give the desired UPE resins Inhibitors can be added to the monomer for extending storage stability of the resin.

Examples of unsaturated carboxylic acids and corresponding anhydrides useful in the present process include maleic acid, fumaric acid, itaconic acid and maleic anhydride. In addition other acids, anhydrides or esters of the acids can be added to modify the chemical composition. Non-limiting examples of such acids and anhydrides include phthalic acid, isophthalic acid, terephthalic acid, tetrahydrophthalic anhydride, phthalic anhydride, nadic anhydride, methylnadic anhydride, hexahydrophthalic anhydride, dimethyl terephthalate and the like. Maleic acid and maleic anhydride are used in illustrative embodiments.

Other materials commonly used in the synthesis of unsaturated polyester resins, such as solvents, isomerization and/or condensation catalyst, promoters, etc. can be used in the process of the invention. Examples of solvents are those commonly known in the art and include but are not limited to hexane, cyclohexane, benzene, toluene, xylene, and mixtures of solvents. Commonly used inhibitors include hydroquinone, p-benzoquinone, di-t-butylhydroquinone, t-butylcatechol, phenothiazine, and the like. Catalysts used to promote the condensation reaction include p-toluene sulfonic acid, methane sulfonic acid, zinc salts (e.g. acetate), organotin compounds (dibutyl tin oxide) and other materials known to those skilled in the art. Isomerization catalysts include organic amines such as morpholine and piperidine.

Commercially available UPE resins used in this process include Pedigree® 600 Styrene, Pedigree® 600 VT and Pedigree® 70 VT. All were uncatalyzed but can be cured with conventional peroxide initiators such as TBP or dicumylperoxide. The present disclosure is not limited to UPE resins used in electrical insulating materials but could also be used in molding materials and any other resin systems using UPE resins with reactive monomers such as, for example, styrene, vinyltoluene, diallylphthalate, acrylates, methacrylates, trimethylolpropane triacrylate, acrylated bisphenol A, methyl methacrylate, hydroxyethyl methacrylate, methyl acrylate, butanedioldimethacrylate, hexanedioldiacrylate, vinyl pyrrolidone, diallylmaleate, and butylvinylether.

In general, the process of catalyzing unsaturated polyesters may be carried out by two techniques. The first process involves mixing the metal-organic titanium or zirconium compound into the resin either by means of mixing blade or dissolution with time and temperature. Some derivatives are more soluble than others and require less energy to dissolve the material into the UPE resin while others require more energy to achieve dissolution. The benzopinacol can then be added with mixing. Benzopinacol can also be pre-dissolved/dispersed in another liquid prior to adding to the UPE resin solution. According to certain embodiments, the metal-organic titanium compound can be added to the UPE resin material at levels of about 0.001 to about 10%. According to certain embodiments, the benzopinacol can be added to the UPE resin material at levels of about 0.1 to about 10%. According to alternative embodiments, the initiator system loading level is about 1 to about 2% to UPE resin material.

The second method involves mixing the metal-organic titanium or zirconium compound into the resin system as part A and the benzopinacol into a separate portion of the resin as part B. The ratio of part A to part B can be adjusted by the concentration of the benzopinacol and metal-organic titanium/zirconium compound so that the mix ratio gives the right concentration of initiator package to resin/monomer. The advantageous use of a 2-part system is that part A and part B both have good shelf stability. With peroxide based systems with high reactivity this is not possible due to short stability times. For ease of use, customers typically want a mix ratio close to 1:1 for a 2-part system. According to certain embodiments, the metal-organic titanium compound can be added to the UPE resin material at levels of about 0.001 to about 10%. According to certain embodiments, the benzopinacol can be added to the UPE resin material at levels of about 0.1 to about 10%.

The following examples are set forth to describe a method of synthesizing various illustrative embodiments of the titanium or zirconium alkoxide of benzopinacol in further detail and to illustrate exemplary method of preparation and use of the initiator. The following examples following should not be construed as limiting the initiator, the methods of preparing the initiator or method of using the initiator in polymerization reactions in any manner.

Titanium Alkoxide of Benzopinacol Initiator Synthesis
  Synthesis of Initiator:
  Tetrabutyltitanate, 0.053 moles (18.02 grams), benzopinacol, 0.053 moles (19.4 grams), and hexylene glycol, 0.027 moles (3.127 grams), were dissolved in 250 grams of ethyl acetate and 250 grams of toluene and mixed about two hours at room temperature. Ethyl acetate, toluene and evolved butanol were removed by vacuum distillation (rotary evaporator) at 50° C. until the material was reduced to a yellow-brown liquid. 500 grams of toluene were added and the rotovap procedure was repeated. Another 500 grams of toluene was added and the rotovap procedure was again repeated. The result was a yellow-brown liquid/paste material, which was then dried at 40° C. to a somewhat thicker paste.

Zirconium Alkoxide of Benzopinacol Initiator Synthesis

Synthesis of Initiator:

Tetraisopropylzirconate, 0.053 moles (17.3 grams), benzopinacol, 0.053 moles (19.4 grams), and hexylene glycol, 0.027 moles (3.127 grams), were dissolved in 250 grams of ethyl acetate and 250 grams of toluene and mixed about two hours at room temperature. Ethyl acetate, toluene and evolved i-propanol were removed by vacuum distillation (rotary evaporator) at 50° C. until the material was reduced to a clear liquid. 500 grams of toluene were added and the rotovap procedure was repeated. Another 500 grams of toluene was added and the rotovap procedure was again repeated. The result was a colorless solid, which was then dried at 40° C.

Polymerization Example 1

Tetra n-butyltitanate and benzopinacol were mixed into Pedigree 600S at 0.3% each and mixed with a cowles blade until a dispersion was obtained. The dispersion was tested for gel time with a Sunshine gel time meter at various temperatures. The material was tested with a Q200 Modulated DSC. The results are shown in Table 1.

Polymerization Example 2

Tetra n-butyltitanate and benzopinacol were mixed into Pedigree 600S at 2.0% each and mixed with a cowles blade was tested for gel time with a Sunshine gel time meter at various temperatures. The results are shown in Table 1.

Polymerization Example 4

Tetra n-butyltitanate and benzopinacol were mixed into Pedigree 600S at 0.1% and 1.0% respectively and mixed with a cowles blade until a dispersion was obtained. The dispersion was tested for gel time with a Sunshine gel time meter at various temperatures. The results are recorded in Table 1.

Polymerization Example 5

Tetra n-butyltitanate and benzopinacol were mixed into Pedigree 600S at 0.01% and 1.0% respectively and mixed with a cowles blade until a dispersion was obtained. The dispersion was tested for gel time with a Sunshine gel time meter at various temperatures. The results are shown in Table 1.

Comparative Polymerization Example 1

Benzopinacol was blended into Pedigree 600S at 2% with a cowles blade until a dispersion was obtained. 25 grams of this dispersion was blended with 25 grams of Pedigree 600S to obtain a benzopinacol concentration of 1%. The material was tested with a Sunshine gel time meter at various temperatures. The material was also tested with a Q200 Modulated DSC. The results are shown in Table 1 and a second run in Table 4.

Comparative Polymerization Example 2

Tetra n-butyltitanate was blended into Pedigree 600S at 0.3% until a homogenous mixture was obtained. The material was tested with a Sunshine gel time meter at various temperatures. The results are shown in Table 1.

TABLE 1

| | Example 1 | Example 2 | Example 3 | Example 4 | Example 5 | Comparative Example 1 | Comparative Example 2 |
|---|---|---|---|---|---|---|---|
| Resin System | Pedigree 600S | Pedigree 600S | Pedigree 600S | Pedigree 600S | Pedigree 600S | Pedigree 600S | Pedigree 600S |
| Benzopinacol % | 0.3 | 2 | 1 | 1 | 1 | 1 | 0 |
| TNBT % | 0.3 | 2 | 0.2 | 0.1 | 0.01 | 0 | 0.3 |
| 125 C Sunshine gel | 3.1 | <3 | 2.5 | 2.75 | 3.8 | 5 | >30 |
| 100 C Sunshine gel | 4.6 | <3 | 2.5 | 4.15 | 8.5 | 17.1 | >30 |
| 90 C Sunshine gel | 11 | <3 | 5.8' | 8.4' | 18.4' | 35.6' | >100 |
| 80 C Sunshine gel | 32.8' | 3.3 | 9.5' | 16.5' | 43.1' | 94.1' | >100 |
| DSC onset ° C. | 116 | 67 | | | | 123.6 | |
| Peak Max ° C. | 149 | 97 | | | | 136.6 | |
| Joules/gram | 300 | 318 | | | | 357.4 | |
| Barber Colman hardness | | | 91 | 91 | 92 | 92 | | until a dispersion was obtained. The dispersion was tested for gel time with a Sunshine gel time meter at various temperatures. The material was tested with a Q200 Modulated DSC. The results are shown in Table 1.

Polymerization Example 3

Tetra n-butyltitanate and benzopinacol were mixed into Pedigree 600S at 0.2% and 1.0% respectively and mixed with a cowles blade until a dispersion was obtained. The dispersion Polymerization Example 6

Initiator 1 (titanium alkoxide or benzopinacol) was blended into Pedigree 600S at 1% and mixed with a laboratory mixer until homogenous. The mixture was tested with a Sunshine gel time meter at various temperatures. The results are shown in Table 2.

Polymerization Example 7

Initiator 1 (titanium alkoxide or benzopinacol) was blended into Pedigree 600S at 2% and mixed with a laboratory mixer until homogenous. The mixture was tested with a Sunshine gel time meter at various temperatures. The results are shown in Table 2.

Polymerization Example 8

Initiator 1 (titanium alkoxide or benzopinacol) was blended into Pedigree 70VT at 1% and mixed with a laboratory mixer until homogenous. The mixture was tested with a Sunshine gel time meter at various temperatures. The results are shown in Table 2.

TABLE 2

|  | Example 6 | Example 7 | Example 8 |
|---|---|---|---|
| Resin System | Pedigree 600S | Pedigree 600S | Pedigree 70 VT |
| Titanium Alkoxide of Benzopinacol % | 1% | 2% | 1% |
| 125 C. Sunshine gel | 3.4 | 2.3' | 1.93' |
| 100 C. Sunshine gel | 7.8' | 4.2' | 1.93' |
| 90 C. Sunshine gel | 11.2' | 5.7' | 4.6' |
| 80 C. Sunshine gel | 23.3' | 7.3' | 20.9' |

The following titanates were evaluated in illustrative polymerization processes.

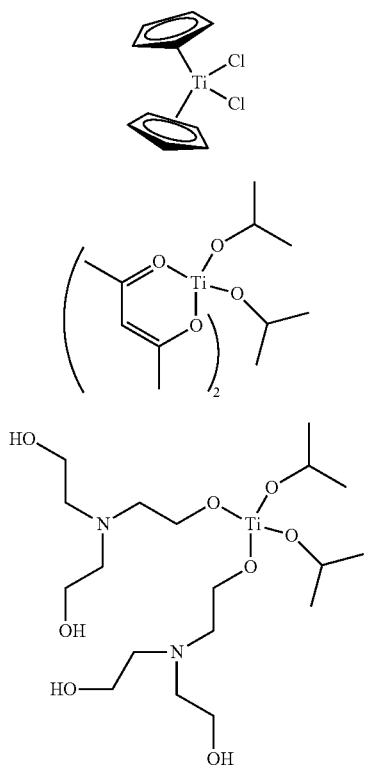

Polymerization Example 9

Part A: Benzopinacol was blended into Pedigree 600S at 2% and mixed with a cowles blade until a dispersion was obtained.

Part B: Titanate #1 was blended into Pedigree 600S at 2% and mixed with a cowles blade until a dispersion was obtained.

Equal parts by weight of Part A and B were blended until homogenous. The mixture was tested with a Sunshine gel time meter at various temperatures. The results are shown in Table 3.

Polymerization Example 10

Benzopinacol was blended into Pedigree 600S at 2% and mixed with a cowles blade until a dispersion was obtained. 25 grams of this dispersion were blended with 12.5 grams of Pedigree 600S and 0.25 grams of Titanate #2 and mixed until homogenous to obtain a blend that was 1% benzopinacol and 1% Titanate #2. This blend was tested with a Sunshine gel time meter at various temperatures. The results are shown in Table 3.

Polymerization Example 11

A polymerization reaction was carried out as set forth in Polymerization Example 10, except that Titanate #2 was replaced by Titanate #3. This blend was tested with a Sunshine gel time meter at various temperatures. The results are shown in Table 3.

TABLE 3

|  | Example 9 | Example 10 | Example 11 |
|---|---|---|---|
| Resin System | Pedigree 600S | Pedigree 600S | Pedigree 600S |
| Titanate (#) @ 1% | (1) | (2) | (3) |
| Benzopinacol | 1% | 1% | 1% |
| 125 C. Sunshine gel | 3.5' | 0.8' | 2.8' |
| 100 C. Sunshine gel | 4.2' | 0.8' | 5.6' |
| 90 C. Sunshine gel | 7.1' | 1.3' | 6.7' |
| 80 C. Sunshine gel | 11.7' | 1.4' | 9.5' |

Polymerization Example 12

Part A: Benzopinacol was blended into Pedigree 600S at 2% and mixed with a cowles blade until a dispersion was obtained.

Part B: Titanate #1 was blended into Pedigree 600S at 1% until a dispersion was obtained.

15 grams of Pedigree 600S were blended with 25 grams of Part A and 10 grams of Part B to obtain a mixture that was 1% benzopinacol and 0.2% Titanate #1. This blend was tested with a Sunshine gel time meter at various temperatures. The results are shown in Table 4.

Polymerization Example 13

A polymerization reaction was carried out as set forth in Polymerization Example 12 except that 20 grams of Pedigree 600S, 25 grams of part A, and 5 grams of Part B were blended to give a mixture that was 1% benzopinacol and 0.1% Titanate #1. This blend was tested with a Sunshine gel time meter at various temperatures. The results are shown in Table 4.

Polymerization Example 14

A polymerization reaction was carried out as set forth in Polymerization Example 12 except that 24.5 grams of Pedigree 600S, 25 grams of part A, and 0.5 grams of Part B were blended to give a mixture that was 1% benzopinacol and 0.01% Titanate #1. This blend was tested with a Sunshine gel time meter at various temperatures. The results are shown in Table 4.

TABLE 4

| Example | Example 12 | Example 13 | Example 14 | Comparative Example 1 |
| --- | --- | --- | --- | --- |
| Resin System | Pedigree 600S | Pedigree 600S | Pedigree 600S | Pedigree 600S |
| Part A (benzopinacol) | 1% | 1% | 1% | 1% |
| Part B (titanocene dichloride) | 0.20% | 0.10% | 0.01% | 0 |
| 100 C. Sunshine gel | 5.7' | 5.5' | 6.5' | 17.5' |
| 125 C. Sunshine gel | 3.9' | 3.8' | 4.1' | 5.0' |

Polymerization Example 15

Part A: Benzopinacol was blended into Pedigree 600S at 2% and mixed with a cowles blade until a dispersion was obtained.

Part B: Tetra n-butyltitanate was blended into Pedigree 600S at 2% and mixed until homogenous.

100 grams of Part A, 100 grams of Part B were blended and mixed until homogenous to give a mixture that was 1% benzopinacol and 1% tetra n-butyltitanate. The mixture was tested with a Sunshine gel time meter at various temperatures and observed for stability at room temperature and at 50° C. Results are recorded in Table 5.

Polymerization Example 16

A polymerization was carried out as set forth in Polymerization Example 15 except that Part A: Benzopinacol was blended into Pedigree 600S at 2% and mixed with a cowles blade until a dispersion was obtained.

Part B: Tetra n-butyltitanate was blended into Pedigree 600S at 4% and mixed until homogenous.

100 grams of Part A were blended with 100 grams of part B to give a mixture that was 1% benzopinacol and 2% tetra n-butyltitanate. Results are recorded in Table 5.

Polymerization Example 17

A polymerization was carried out as set forth in Polymerization Example 15 except that Part A: Benzopinacol was blended into Pedigree 600S at 2% and mixed with a cowles blade until a dispersion was obtained.

Part B: is tetra n-butyltitanate 98 grams of Part A were blended with 2 grams of Part B to give a mixture that was 2% benzopinacol and 2% tetra n-butyltitanate. Results are shown in Table 5.

TABLE 5

| Example | Example 15 | Example 16 | Example 17 | Comparative Example 1 |
| --- | --- | --- | --- | --- |
| Resin System | Pedigree 600S | Pedigree 600S | Pedigree 600S | Pedigree 600S |
| Part A (benzopinacol) | 1% | 1% | 2% | 1% |
| Part B (tetrabutyl-titanate) | 1% | 2% | 2% | 0 |
| 100 C. Sunshine gel | 3.2' | 3.4' | 2.6' | 15' |
| 90 C. Sunshine gel | 4.0' | 3.6' | 2.9' | 35.6' |
| 80 C. Sunshine gel | 6.0' | 4.7' | 3.5' | 94.1' |
| RT gel Time | >4 weeks | <1 day | <3 hours | >4 weeks |

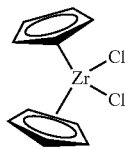

4

Polymerization Example 18

Part A: Benzopinacol was blended into Pedigree 600S at 2% and mixed with a cowles blade until a dispersion was obtained.

Part B: Zirconate #4 was blended into Pedigree 600S at 2% and mixed with a cowles blade until a dispersion was obtained.

Equal parts by weight of Part A and B were blended until homogenous. The mixture was tested with a Sunshine gel time meter at various temperatures. The results are recorded in Table 6.

TABLE 6

| Example | Example 18 |
| --- | --- |
| Resin System | 600S |
| benzopinacol % | 1% |
| zirconocene dichloride % | 1% |
| 125 C. sunshine gel | 4.8' |
| 100 C. sunshine gel | 6.0' |

While the methods of preparation and use have been described in connection with various illustrative embodiments, it is to be understood that other similar embodiments may be used or modifications and additions may be made to the described embodiments for performing the same function disclosed herein without deviating there from. The embodiments described above are not necessarily in the alternative, as various embodiments may be combined to provide the desired characteristics. Therefore, the preparation and methods should not be limited to any single embodiment, but rather construed in breadth and scope in accordance with the recitation of the appended claims.

The invention claimed is:

1. A polymerization initiator comprising the reaction product of a metal-organic compound, wherein said metal is titanium or zirconium, and pinacol compound of the following general formula:

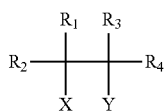

wherein R₁ and R₃ are the same or different substituted or unsubstituted aromatic groups;

wherein R₂ and R₄ are the same or different substituted or unsubstituted aliphatic or aromatic groups; and wherein X and Y are the same or different and may comprise hydroxyl, alkoxy, or aryloxy groups.

2. The polymerization initiator of claim 1 comprising the reaction product of said metal-organic compound, wherein said metal is titanium, and said pinacol.

3. The polymerization initiator of claim 1 comprising the reaction product of said metal-organic compound, wherein said metal is zirconium, and said pinacol.

4. The polymerization initiator of claim 2 wherein the pinacol comprises benzapincol of the following structure:

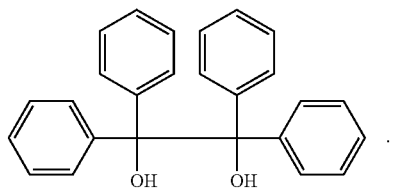 [SMILES: OC(c1ccccc1)(c1ccccc1)C(O)(c1ccccc1)c1ccccc1]

5. The polymerization initiator of claim 3 wherein the pinacol comprises benzapincol of the following structure:

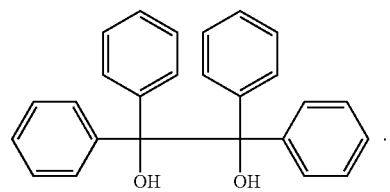 [SMILES: OC(c1ccccc1)(c1ccccc1)C(O)(c1ccccc1)c1ccccc1]

6. The polymerization initiator of claim 1 comprising the following general formula:

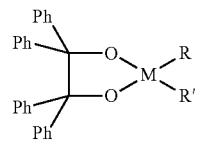

wherein M comprises a metal selected from titanium and zirconium; and wherein R and R' comprise an organic moiety.

7. The polymerization initiator of claim 6 comprising the following general formula:

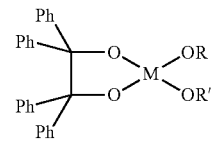

wherein M comprises a metal selected from titanium and zirconium; and wherein R and R' comprise an organic moiety.

8. The polymerization initiator of claim 1, wherein said polymerization initiator comprises a titanium alkoxide of benzopinacol of the following chemical structure:

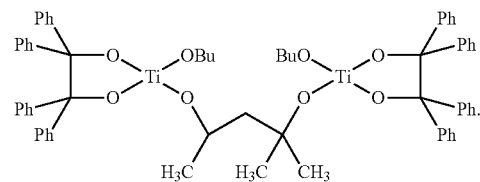

9. The polymerization initiator of claim 1, wherein said polymerization initiator comprises a zirconium alkoxide of benzopinacol of the following chemical structure:

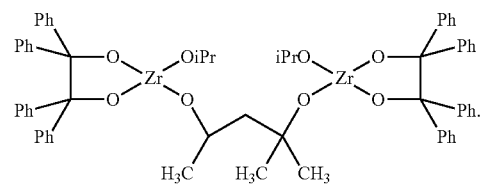

10. A polymerization process comprising:
adding a polymerization initiator comprising the reaction product metal-organic compound, wherein said metal is titanium or zirconium, and a pinacol to a reactive monomer, or an unsaturated polymer, or a mixture of unsaturated polymer and reactive monomer; and
polymerizing said reactive monomer and/or unsaturated polymer.

11. The polymerization process of claim 10, wherein said pinacol compound comprises the following general formula:

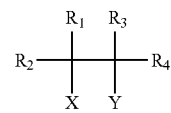

wherein R₁ and R₃ are the same or different substituted or unsubstituted aromatic groups;

wherein R₂ and R₄ are the same or different substituted or unsubstituted aliphatic or aromatic groups; and wherein X and Y are the same or different and comprise hydroxyl, alkoxy, or aryloxy groups.

12. The polymerization process of claim 11, wherein said polymerization initiator comprises the reaction product of a metal-organic compound, wherein said metal is titanium, and said pinacol.

13. The polymerization process of claim 11 wherein said polymerization initiator comprises the reaction product of a metal-organic compound, wherein said metal is zirconium, and said pinacol.

14. The polymerization process of claim 12 wherein the pinacol comprises benzapincol of the following structure:

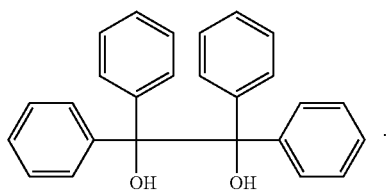 [SMILES: OC(c1ccccc1)(c1ccccc1)C(O)(c1ccccc1)c1ccccc1]

15. The polymerization process of claim 13 wherein the pinacol comprises benzapincol of the following structure:

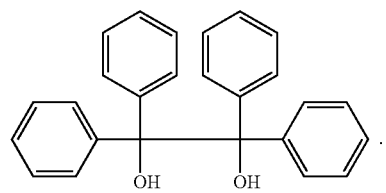 [SMILES: OC(c1ccccc1)(c1ccccc1)C(O)(c1ccccc1)c1ccccc1]

16. The polymerization process of claim 10 wherein said polymerization initiator comprises the following general formula:

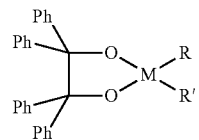

wherein M comprises a metal selected from titanium or zirconium; and
wherein R and R' comprise an organic moiety.

17. The polymerization process of claim 10 wherein said polymerization initiator comprises the following general formula:

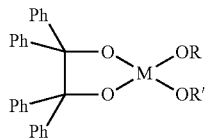

wherein M comprises a metal selected from titanium or zirconium; and
wherein R and R' comprises an organic moiety.

18. A polymerization process comprising:
separately adding (i) metal-organic compound, wherein said metal is titanium or zirconium, and (ii) a pinacol compound to a reactive monomer, or an unsaturated polymer, or a mixture of unsaturated polymer and reactive monomer; and
polymerizing said reactive monomer and/or unsaturated polymer.

19. The polymerization process of claim 18 comprising:
adding a metal-organic compound, wherein said metal is titanium or zirconium, to a reactive monomer, or an unsaturated polymer, or a mixture of unsaturated polymer and reactive monomer to prepare a first mixture;
adding a pinacol compound to a reactive monomer, or an unsaturated polymer, or a mixture of unsaturated polymer and reactive monomer to prepare a second mixture;
combining said first mixture and said second mixture; and
polymerizing said reactive monomer and/or unsaturated polymer present in said combined first and second mixture.

20. The polymerization process of claim 18, wherein said metal-organic compound comprises the following chemical structure:

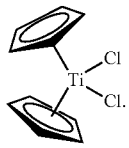

21. The polymerization process of claim 18, wherein said metal-organic compound comprises the following chemical structure:

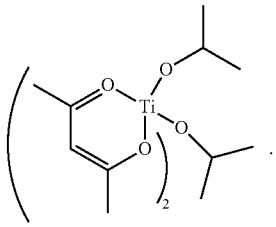

22. The polymerization process of claim 18, wherein said metal-organic compound comprises the following chemical structure:

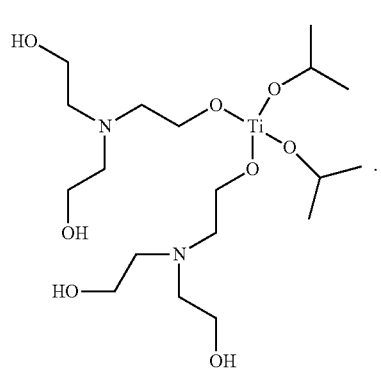

23. The polymerization process of claim 18, wherein said metal-organic compound comprises the following chemical structure:

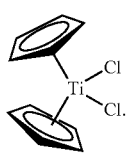

* * * * *

UNITED STATES PATENT AND TRADEMARK OFFICE
CERTIFICATE OF CORRECTION

| | | |
|---|---|---|
| PATENT NO. | : 8,674,041 B2 | Page 1 of 1 |
| APPLICATION NO. | : 13/554235 | |
| DATED | : March 18, 2014 | |
| INVENTOR(S) | : Thomas J. Murray et al. | |

It is certified that error appears in the above-identified patent and that said Letters Patent is hereby corrected as shown below:

In the Claims

Claim 23 (Column 16, line 60) should read as follows:

23. The polymerization process of claim 18, wherein said metal-organic compound comprises the following chemical structure:

Signed and Sealed this
Twenty-seventh Day of May, 2014

Michelle K. Lee
*Deputy Director of the United States Patent and Trademark Office*